United States Patent
Ishibashi

(10) Patent No.: US 8,367,324 B2
(45) Date of Patent: Feb. 5, 2013

(54) METHOD FOR JUDGING CHANGE IN PROBE-BEARING SUBSTRATE, PROBE-BEARING SUBSTRATE AND DETECTING APPARATUS

(75) Inventor: Tohru Ishibashi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 938 days.

(21) Appl. No.: 10/978,582

(22) Filed: Nov. 2, 2004

(65) Prior Publication Data

US 2005/0106613 A1    May 19, 2005

(30) Foreign Application Priority Data

Nov. 17, 2003  (JP) ................................. 2003-387003

(51) Int. Cl.
*C12Q 1/68* (2006.01)
*C12P 19/34* (2006.01)
*C12M 1/34* (2006.01)
*C07H 21/02* (2006.01)
*C07H 21/04* (2006.01)

(52) U.S. Cl. .... 435/6.1; 435/6.11; 435/91.1; 435/287.2; 536/23.1; 536/24.3; 536/24.33

(58) Field of Classification Search ............... 435/6, 7.1, 435/91.1, 6.1, 6.11, 287.2; 436/94, 501; 536/23.1, 24.3, 24.33; 530/300, 350; 424/130.1, 424/178.1, 184.1
See application file for complete search history.

(56) References Cited

U.S. PATENT DOCUMENTS

| | | | |
|---|---|---|---|
| 4,169,811 A | 10/1979 | Yoshikawa et al. | 252/408 |
| 5,143,854 A | 9/1992 | Pirrung et al. | 436/518 |
| 5,422,242 A * | 6/1995 | Young | 435/6 |
| 5,688,642 A | 11/1997 | Chrisey et al. | 435/6 |
| 5,824,799 A * | 10/1998 | Buechler et al. | 540/128 |
| 5,908,746 A | 6/1999 | Suzuki et al. | 435/6 |
| 6,015,880 A | 1/2000 | Baldeschwieler et al. | 530/333 |
| 6,017,742 A | 1/2000 | Takenishi et al. | 435/180 |
| 6,761,877 B2 * | 7/2004 | Barbera-Guillem | 424/9.6 |
| 6,902,900 B2 * | 6/2005 | Davies et al. | 435/6 |
| 7,101,671 B2 * | 9/2006 | Gao | 435/6 |
| 2003/0027129 A1 | 2/2003 | Warner et al. | 435/5 |
| 2004/0005620 A1 | 1/2004 | Okada et al. | 435/6 |

FOREIGN PATENT DOCUMENTS

| | | |
|---|---|---|
| EP | 0 895 082 | 2/1999 |
| JP | 53-120493 | 10/1978 |
| JP | 56-060349 | 5/1981 |
| JP | 64-010172 | 1/1989 |
| JP | 3-19536 | 3/1991 |
| JP | 5-10624 | 2/1993 |
| JP | 6-018676 | 1/1994 |
| JP | 8-023975 | 1/1996 |
| JP | 8-334509 | 12/1996 |
| JP | 10-293183 | 11/1998 |
| JP | 11-014616 | 1/1999 |
| JP | 11-140339 | 5/1999 |
| JP | 2000-039429 | 2/2000 |
| JP | 2001-178442 | 7/2001 |
| JP | 2001-281052 | 10/2001 |
| WO | 95/25116 | 9/1995 |
| WO | 03/056007 | 7/2003 |
| WO | 2004/010144 | 1/2004 |

OTHER PUBLICATIONS

Attached definition for DNA melting temperature.*
Maniatis et al., Molecular Cloning: a laboratory manual, pp. 468 and 469, 1982. Published by Cold SPring Harbor Laboratory.*
Biotinylated DNA standard. Printed on Sep. 1, 2012.*
The definition for "room temperature". Printed on Sep. 1, 2012.*
Temperature Indicator Labels. Printed on Sep. 1, 2012.*
Kaede (protein) from Wikipedia, the free encyclopedia. Printed on Sep. 1, 2012.*
European Office Action dated Sep. 17, 2012 in European Application No. 04257095.2.

* cited by examiner

*Primary Examiner* — Frank W Lu
(74) *Attorney, Agent, or Firm* — Fitzpatrick, Cella, Harper & Scinto

(57) ABSTRACT

A probe-bearing substrate in which a probe capable of specifically binding to a target substance is immobilized on a substrate, characterized in that the probe-bearing substrate further includes a device for detecting an environmental change that may cause a change in the probe-bearing substrate such as probe deterioration or change in a substrate-protecting member.

7 Claims, 2 Drawing Sheets

METHOD FOR JUDGING CHANGE IN PROBE-BEARING SUBSTRATE, PROBE-BEARING SUBSTRATE AND DETECTING APPARATUS

BACKGROUND OF THE INVENTION

1. Field of the Invention

The present invention relates to a method for judging a level of deterioration of target-specific probes immobilized on a substrate, and a level of changes in a probe-bearing substrate including changes in a protective member protecting the probe or the like, a probe-bearing substrate having a device effective for judging changes in the probe-bearing substrate including changes in the protective member, and a system for judging changes in a probe-bearing substrate including changes in the protective member.

2. Related Background Art

An example of the probe-bearing substrate is a DNA chip. The DNA chip is a high-density chip in which a plurality of DNA fragments or oligonucleotides that are useful for simultaneous analysis of genetic expression, mutation or polymorphism are arranged and immobilized as probes on a solid surface. For example there have been disclosed a solid-phase oligonucleotide array prepared by a photolithographic method (U.S. Pat. No. 5,688,642) and a method for producing a solid-phase DNA probe array by an ink jet method (WO95/25116).

A process for detecting a target substance generally includes a hybridization reaction to cause binding between the target substance labeled with a fluorescent material etc. and a target-specific probe on the solid probe array. Such a hybridization reaction is achieved by contacting or immersing the solid probe array in a solution containing the target substance applying heat. The reaction conditions such as the concentration of the solution and reaction temperature may vary according to the combination of the probe and the target substance. Then, whether binding between the probe and the target substance has occurred or not is observed using an apparatus such as a fluorescence detector.

SUMMARY OF THE INVENTION

In general, DNA is decomposed by ultraviolet light or heat, so that the probe deteriorates and loses the ability to hybridize with a target nucleic acid when it is exposed to prolonged ultraviolet light irradiation such as sunlight or is stored at a high temperature. Also, the amount of the probe immobilized in the thus-prepared probe array is very small, so that it is often difficult to measure the amount or activity of such probe in a non-destructive manner.

Thus, one object of the present invention is to provide a method for judging loss of probe functions owing to various environmental conditions such as UV and high temperature.

The substrate may be provided with a protective member for the purpose of protecting the probe. However, such protective member may change with the above-mentioned factors.

Thus another object of the present invention is to provide a method for easily judging such changes.

The present invention provides a probe-bearing substrate in which a probe capable of specifically binding to a target substance is immobilized on a substrate, characterized in that the probe-bearing substrate further includes a device for detecting an environmental change that may cause a change in the probe-bearing substrate.

The present invention also provides a method for judging presence/absence of a change in the probe-bearing substrate or a level of such change, utilizing the device provided in or on the probe-bearing substrate.

The present invention further provides a system including acquisition means which acquires information on an amount of an environmental change from the device provided in or on the probe-bearing substrate, and judgment means which judges presence/absence of a change in the probe-bearing substrate, based on the environmental change information acquired by the acquisition means.

According to the present invention, a device for detecting an environmental change that induces changes in the probe-bearing substrate is provided on a substrate to determine the presence or absence or degree of the change in the probe-bearing substrate, i.e., probe deterioration, and a change in a protective member provided on the substrate, thereby facilitating quality control during the manufacture, distribution and storage processes, and confirmation of the probe function.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

Figure 1:
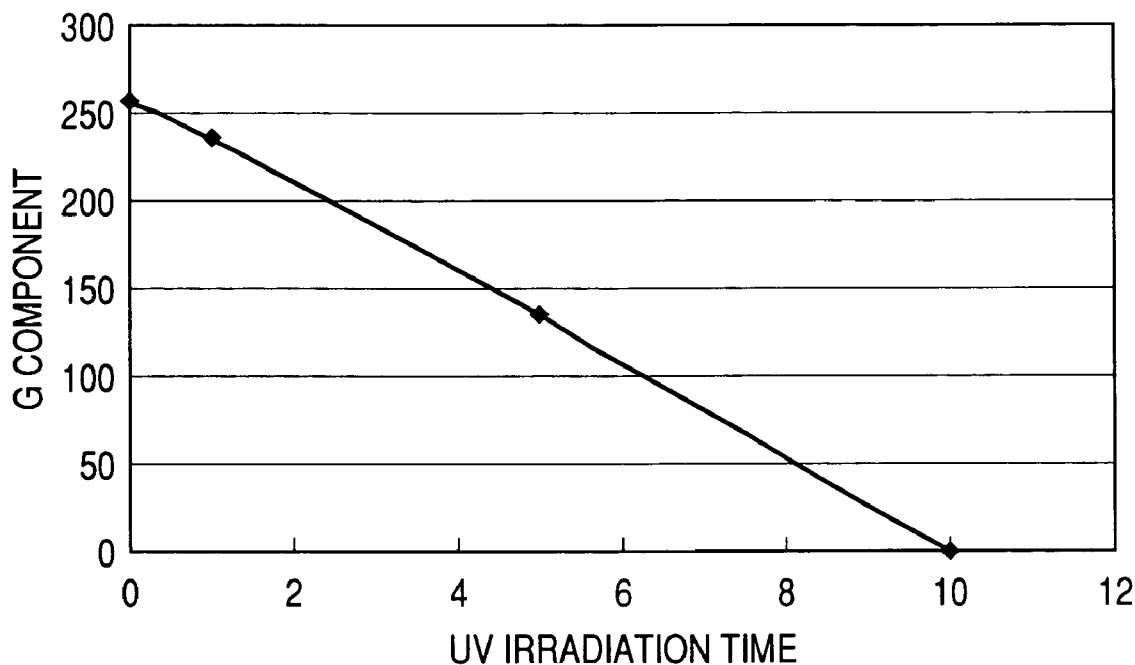
FIG. 1 shows a relationship between the period of UV irradiation and the G component intensity of a UV label.

Preferred embodiments of the present invention will not be described in detail in accordance with the accompanying drawings.

The present invention provides a judging method for determining the presence or absence or level of any change relating to the performance of the probe-bearing substrate on which a probe that can bind to a target substance specifically is immobilized. The present invention also includes a probe-bearing substrate enabling such a determination method, and a system for calculating the level of change of the probe-bearing substrate utilizing such a determining method. The change in the probe-bearing substrate includes deterioration in the probe and changes in the protective member provided for protecting the probe.

A substrate for immobilizing the probe is not particularly limited as long as it is capable of immobilizing probes and does not hinder the detection or isolation of the target substance. The substrate can be, for example, glass, resin, metal or a hollow fiber. In case of the DNA chip, for example, a glass substrate or a plastic substrate, particularly an alkali-free glass substrate or a quartz substrate not containing alkali components, is preferable in consideration of detection of the target substance or wide applicability.

Various methods are known for immobilizing a probe on the substrate. More specifically, there are two general immobilization methods: a method synthesizing the probe on the substrate, and a method applying a probe prepared in advance to the substrate using a pin or stamp.

To synthesize a probe on the substrate, as described in U.S. Pat. No. 5,143,854, a monomer having a removable protective group is bonded onto a predetermined site on a substrate where a protective group has been removed by using an activator and such a process is repeated, thereby synthesizing polymers of various arrangements on the substrate.

To immobilize a probe prepared in advance onto a substrate, as described in Japanese Patent Application Laid-Open No. H08-23975, a biologically active substance reactive with the carbodiimide group is contacted with a immobilizing material comprised of a polymer having a carbodiimide group borne on the substrate. Also Japanese Patent Application Laid-Open No. H08-334509 describes a method for detecting a biologically active substance where a substance is immobilized onto a compound having a carbodiimide group via the carbodiimide group.

Also Japanese Patent Application Laid-Open No. 2001-178442 discloses a method of immobilizing a DNA fragment onto a solid carrier surface by contacting a solution of a DNA fragment having a terminal thiol group and the carrier bearing a linear molecule having a reactive substituent capable of forming a covalent bond with the thiol group, thereby forming a covalent bond between the DNA fragment and the linear molecule. Specifically, the reactive substituent capable of forming a covalent bond with the thiol group has a group selected from a maleimidyl group, an $\alpha,\beta$-unsaturated carbonyl group, an $\alpha$-halocarbonyl group, a halogenated alkyl group, an aziridine group and a disulfide group.

Various probe-immobilizing methods are known even if limited to DNA fragment immobilization, but the present invention is applicable to any type of probes and immobilization methods.

Probes of the probe-bearing substrate generally lose the probe function by the action of, depending on the type of the probe, temperature, ultraviolet light or oxygen. Such phenomenon will hereinafter be called "deterioration". Heretofore, no simple method for judging or determining the degree such deterioration has been available. According to the invention, the substrate is provided with a device for detecting a factor that causes such deterioration, and a level of such a factor is measured prior to the use of the probe-bearing substrate, thereby determining the deterioration degree of the probe. Factors for the probe deterioration include exposure to UV irradiation, condensation, temperature change, oxidation and pH change, but not limited thereto.

The devices for detecting such deterioration factors are described below.

When the factor is ultraviolet light, there are a UV-detecting material comprised of a dimeric quinone compound formulated in polyolefin resin which discolors on reduction with UV irradiation and restores color when it is oxidized by heating (Japanese Patent Application Laid-Open No. 2001-281052), a liquid UV detecting composition comprised of polyvinyl chloride of a low polymerization degree and a colored or colorless dye as essential components, which colored or colorless dye can cause conspicuous change in color hue of density under irradiation in near UV region (Japanese Patent Publication No. H03-19536), as well as commercially available UV detecting materials (for example "UV label" (trade name), manufactured by Nichiyu Giken Kogyo Co.).

Since the degree of the influence of ultraviolet light may vary with the type of the probe, it is preferable to adjust the sensitivity of the device material to be optimum for the probe, and the present invention does not restrict the sensitivity or type of the UV-detecting material.

When the factor is temperature, a temperature indicating material that changes color hue or color density with temperature is preferably used. Specific examples include, a rewritable electron-donating color-developing compound based on non-crystalline-crystalline transition or phase separation-non phase separation transition such as leucoauramine, diarylphthalide, polyarylcarbinol, acylauramine, rhodamine B lactam, indoline, spiropyran, fluoran, cyanine dye, or crystal violet, and a rewritable electron-accepting compound such as a phenol metal salt, a carboxylic acid metal salt, sulfonic acid, a sulfonate salt, a phosphate salt, a phosphoric acid metal salt, an acidic phosphate ester, an acidic phosphate ester metal salt, a phosphite salt and a phosphite metal salt).

In addition, there is an irreversible temperature indicating material as disclosed in Japanese Patent Application Laid-Open No. H11-140339, which comprises a substrate, a layer containing a colorless or pale-colored basic dye, a color developing agent and a heat-fusible material utilizing 3-(1-n-octyl-2-methylindol-3-yl)-3-(4-diethylamino-2-ethoxyphenyl)-4-azaphthalide or 3,3'-bis(1-n-octyl-2-methylindol-3-yl)phthalide as the basic dye, and 1,2-diphenoxyethane and/or dibenzyl oxalate as the heat melting material. There are also a commercially available temperature indicating material such as "Thermo Paint", "Thermo Label", "Thermo Sheet" and "Thermo Tape" (trade names, all manufactured by Nichiyu Giken Kogyo Co.).

Since the degree of the influence of temperature may vary with the type of the probe, it is preferable to adjust the sensitivity of the device material to be optimum for the probe, and the present invention does not restrict the sensitivity or type of the temperature-detecting material.

It is possible to trace the past record on temperature in more detail by employing plural temperature indicating materials of different characteristics.

Certain probes are oxidized by reacting with oxygen in the air. For such probes, an oxygen detecting material is effective. As an example, there is known an oxygen detecting material which employs a combination of a specific dye such as methylene blue and a reducing agent such as glucose for reducing such dye thereby detecting the presence of oxygen (cf. Japanese Patent Application Laid-Open Nos. S53-120493 and S56-60349).

Also in order to cope with a drawback that glucose is unstable to heat and light, Japanese Patent Application Laid-Open No. 2000-39429 discloses an oxygen detecting material characterized in including at least one selected from cysteine, a salt thereof, an ester thereof and an N-acyl derivative thereof, and a thiazine dye and/or an indigo dye.

Also Japanese Patent Application Laid-Open No. S60-071956 (corresponding to Japanese Publication No. H05-010624) discloses an oxygen indicator utilizing bis(salicylaldehyde)alkylenediimine cobalt (II) or a derivative thereof, and Japanese Patent Application Laid-Open No. S64-10172 discloses an oxygen indicator sheet constituted of a coating film of high molecular cobalt-amine complex and a thermoplastic film layer.

The oxygen detecting materials mentioned above are preferably employed with a regulation of the sensitivity depending on the type of the probe, and are not restricted in the type.

A time indicator is effective for a probe that starts to deteriorate from the time when the package is opened or from the time of preparation of the probe-bearing substrate. As an example, Japanese Patent Application Laid-Open No. H11-14616 discloses a time indicator constituted by laminating a color-changing layer, containing a compound capable of causing a rapid color change by a reaction with oxygen, on one or both sides of a substrate and further laminating an oxygen gas transmission control layer of an oxygen transmission rate of 0.1 to 3000 ml/m$^2$·24 hr·atm·25° C.·100% RH on such color-changing layer.

Also Japanese Patent Application Laid-Open No. H06-18676 discloses a time indicator constructed by forming a composition, obtained by melt kneading of a thermoplastic resin, a volatile electron-accepting organic compound and a hardly volatile electron-donating color-generating organic compound, into a shape in which specific surface area varies in continuous or discontinuous manner.

Furthermore, Japanese Patent Application Laid-Open No. H10-293183 discloses a time indicator constituted of a foamed member or a laminate member which is filled in a space of a container and which shows a delayed shape recovery upon contact with the air.

The time indicators mentioned above are preferably employed with a regulation of the sensitivity depending on the type of the probe, and are not restricted in the type.

For a probe which is deteriorated by the pH, there may be employed a method of attaching a moistened pH indicating sheet, or, in case the probe-bearing substrate is stored in a liquid, a method of dissolving a pH indicator such as phenolsulfonephthalein in the liquid.

It is preferably done to provide a protective member for the purpose of preventing probe deterioration. For example, in case of a DNA chip, the deterioration of the probe can be suppressed by forming a probe protective film such as a film of polyvinyl alcohol (PVA) on a surface on which the probe has been immobilized. The substrate can be used without paying attention to the presence of such PVA film, since the PVA film dissolves in a solution containing the target substance at the time of hybridization. It is however found that, when the DNA chip having such a PVA film is placed under a high temperature, PVA becomes hardened and less soluble. Unless the PVA film dissolves, the hybridization reaction cannot occur properly so that the examination is hindered.

Also in case the protective member serves to protect the probe from a deteriorating factor, for example, being a UV absorbing member, the protective member may be deteriorated to lose its protective ability when it is exposed to a deteriorating factor excessively. In such a case, since the probe may also be deteriorated, it is necessary to detect a change in the protective member.

Therefore, another object of the invention is to provide the substrate with a device for detecting a factor that causes changes in the protective member, thereby judging a level of the factor that induces changes in the protective member prior to the use of the probe-bearing substrate and knowing whether such a substrate can be used properly. Factors that cause the change in the protective member include exposure to UV irradiation, condensation, temperature change, oxidation and pH change, but not limited thereto.

As explained above, various factors exist for inducing changes in the probe-bearing substrate including deterioration of the probe and changes in the protective member. The invention is not limited to the detection of one of such factors but may provide the substrate with a plurality of such devices.

Further, the device for detecting the change in the probe-bearing substrate including the deterioration of the probe and the change in the protective member is preferably irreversible in order to detect the case history, and such a device allows to judge the state of the probe-bearing substrate immediately before the use thereof.

Such a device is not restricted in the shape thereof and may be formed, for example, as a seal, a tape, a sheet, ink, paste, a plate, a rod or granules. There may also be employed a device which changes its shape by a factor such as heat. In consideration of wide applicability, it is preferred to apply an ink-like device or a seal-shaped device to the substrate.

Coating of the substrate may be executed by an ink jet method. Particularly in case of coating with the aforementioned electron-donating color-developing compound of rewritable type by a thermal jet method, the compound is heated above a melting point by heating with the thermal head, then becomes colorless when cooled rapidly and is immobilized to the substrate, thereby realizing a structure which gradually develops color at and above the glass transition point of the system.

A temperature and a time of color development can be controlled by the concentration of a reversible agent.

Also in order to dispense with a work of mounting the device onto the substrate, it is possible to use a substrate formed by mixing such a device into a polymer substrate and to immobilize the probe thereon.

A location where the device for detecting a cause of change is mounted is not restricted as long as such location does not hinder the function of the probe nor the use of the substrate, but, in case of judging the level of deterioration of the probe, it is preferably mounted close to the probe and is preferably mounted directly on the substrate avoiding the portion where the probe is immobilized. It may also be mounted for example on a package, instead of mounting directly on the probe-bearing substrate.

There may also be adopted a method of immobilization by mixing a paste- or ink-shaped device with the probe or by mixing with the protective member.

There is also preferred a device that can be removed at the use, for example, a seal-shaped device adhered with an adhesive of a low adhesive power to realize an easily peelable structure, or a water-soluble device removable by rinsing with water.

The change in the thus-mounted device for detecting the factor that induces changes in the probe-bearing substrate, for example, a change in color or in shape, is examined visually or by using a reading apparatus, and, if a certain change is detected, one can easily know a possibility of probe deterioration or loss of the function of the protective member.

Furthermore, it is possible to quantitatively determine the level of the probe deterioration, by preparing in advance a calibration curve from the degrees of change in the device and the levels of deterioration of the probe, and comparing the actual change in the device with such a calibration curve.

A probe deterioration judging system can be constructed by automating such a process. More specifically, a probe deterioration judging system of the invention comprises means for acquiring information on an environmental change of the probe-bearing substrate from a device provided in such a probe-bearing substrate, and means for judging the presence/absence or the level of a change in the probe-bearing substrate based on the information acquired by the above data-acquisition means. Otherwise, a probe deterioration judging system of the invention can be comprised of reading means which reads an environmental change from a device equipped in the probe-bearing substrate, and calculation means which calculates a level of probe deterioration from the change read by the reading means. More specifically, as explained in the following examples, such a system can be constructed by employing a device capable of showing a color change, reading the color of the device by reading means such as a scanner, separating the color into RGB components of 256 levels each and obtaining the intensity of a predetermined color component such as the R component or G component, and comparing such a color component intensity with a predetermined reference value thereby judging presence/absence of the deterioration in the probe, or by predetermining a relationship between an intensity of a predetermined color component and a level of probe deterioration and calculating the level of probe deterioration from an actually obtained intensity of the color component. Such comparison with the predetermined reference value or calculation of the level of the probe deterioration can be achieved by a program provided in a computer.

Also a system for judging changes in protective member of the invention can be constituted of reading means which reads an environmental change from a device equipped in the probe-bearing substrate, and judging means which judges the presence or absence of a change in the protective member from the environmental change read by the reading means. Otherwise, the judging system for the change in the protective member of the invention can be constituted of reading means which reads the environmental change from a device equipped in the probe-bearing substrate, and calculation means which calculates the level of the change in the protective member from the environmental change read by the reading means. For example, there can be employed a method similar to that in the aforementioned probe deterioration judging system.

Such systems may be provided in a reaction apparatus for reacting a probe immobilized on the substrate and a target substance, and may be so constructed as to display an error message on an error display unit of such a reaction apparatus when a significant deterioration is detected in the probe or the protective member loses its function, thereby suspending the reaction to avoid erroneous diagnosis. Also in case the probe has deteriorated, it is possible to increase the sensitivity by elongating the reaction time or changing reaction conditions such as the reaction temperature.

Furthermore, such systems may be provided on a measuring apparatus for measuring the presence or absence or the amount of a target substance that has reacted with a probe on the substrate. For example, one can prepare in advance a calibration curve of a relationship between the levels of probe deterioration and the measured amounts of the target substance, for example, the fluorescent intensity when the target substance is labeled with a fluorescent material, to correct the actually measured amount of the target substance based on the level of the probe deterioration.

In the following, the present invention will be clarified further by examples.

EXAMPLES

Example 1

Judgment of Probe Deterioration Caused by Ultraviolet Light (1) Preparation of Substrate A glass substrate (a slide) was immersed for 10 minutes in a 1 mol/l aqueous solution of sodium hydroxide heated in advance to 60° C. Subsequently the slide was sufficiently rinsed with pure water to remove sodium hydroxide from the slide. After sufficient rinsing, the slide glass was immersed in pure water and subjected to ultrasonic washing for 10 minutes. After ultrasonic washing, it was sufficiently rinsed in a flow of pure water to eliminate particles sticking to the slide glass. Thereafter, the slide glass was spin dried.

An aminosilane coupling agent (trade name: KBM-603, manufactured by Shin-etsu Chemical Co.) was dissolved to form a 1 wt. % solution, and the slide glass was immersed for 30 minutes in this aqueous solution, then taken out from the solution, rinsed with water and dried in an oven for 1 hour at 120° C. Then, 2.7 mg of N-(6-maleimidocaproyloxy) succinimide (Dojindo Laboratories Co., Ltd.) (abbreviated as EMCS hereinafter) was weighed and dissolved in a mixture of MSO/ethanol (1:1) to a final concentration of 0.3 mg/ml to prepare an EMCS solution. The glass plate subjected to silane coupling treatment was immersed in the EMCS solution at room temperature for 2 hours for the reaction of the amino groups carried on the surface of the glass plate by silane coupling treatment and the carboxyl groups of the EMCS solution. In this condition, the glass plate obtained maleimido groups derived from EMCS on its surface. The glass plate drawn up from the EMCS solution was washed successively with a mixed solvent of dimethylsulfoxide and ethanol and with ethanol and then dried under a nitrogen gas atmosphere.

(2) Probe Synthesis

In the this example, the probe was a single-stranded nucleic acid having a base sequences fully complementary to the entire target nucleic acid to be detected, and capable of detecting the target nucleic acid by specific hybridization with the target. A single-stranded nucleic acid of SEQ ID NO:1 was synthesized by using an automatic DNA synthesizer. At a terminal end of the single-chain DNA, a thiol group was introduced by employing Thiol-Modifier (manufactured by Glen Research Inc.) at the synthesis in the automatic DNA synthesizer. Then, after an ordinary deprotection treatment, DNA was recovered, purified by high-speed liquid chromatography and used in following experiments:

(SEQ ID NO: 1)
5'-HS-(CH$_2$)$_6$-O-PO$_2$-O-ACTGGCCGTCGTTTTACA-3'.

(3) Probe Immobilization

The DNA fragment (SEQ ID NO:1) synthesized in (2) was dissolved to a density of 0.6 OD in an aqueous solution containing 7.5 wt. % of glycerin, 7.5 wt. % of urea, 7.5 wt. % of thiodiglycol and 1 wt. % of acetylene alcohol (trade name: Acetylenol E100, manufactured by Kawaken Fine Chemicals Co.). Here 1 OD means the amount of an oligonucleotide that gives an absorbance 1 when it was dissolved in 1 ml and measured at 260 nm in a cell of an optical path length of 1 cm.

The aqueous solution containing the DNA fragment was spotted onto the slides prepared in (1) by using a bubble jet printer (trade name: BJ-F850, manufactured by Canon Inc.) modified to print on a flat plate, with an about 1 mm distance between the BJ head and the slide glass and a discharge amount of about 4 pl, thereby preparing DNA chips. In this operation, in an observation under a magnifying glass of 15 times, no satellite spots (minute spots generated by splashes when the liquid lands on the solid surface) were observed.

The slides on which the probe-containing solution was spotted were left standing for 10 minutes at the room temperature, then rinsed with a 1M NaCl/50 mM phosphate buffer solution (pH 7.0) and then with pure water, and spin dried.

(4) Mounting of UV-Detecting Material

On each DNA chip prepared in (3), a UV-label type-S (manufactured by Nichiyu Giken Kogyo Co.) was applied in a portion where the probe was not immobilized. The UV-label type-S is white but irreversibly changes to red (pink) under the UV irradiation, with a saturation of coloration at about 250 mJ/cm$^2$.

(5) UV Irradiation

Part of the DNA chip mounted with the UV-detecting material in (4) were subjected to a UV irradiation with an intensity of about 5 mJ/cm$^2$.

(6) Blocking Hybridization Reaction

A bovine serum albumin was dissolved at 1.0 wt. % in a 1M NaCl/50 mM phosphate buffer solution (pH 7.0), and a blocking reaction was executed by immersing DNA chips subjected to the UV irradiation in (5) and DNA chips prepared in (4) (not subjected to UV irradiation) for 2 hours at room temperature.

A labeled DNA fragment was synthesized by bonding rhodamine to the 5'-terminus of a DNA fragment having a sequence complementary to the probe of SEQ ID NO: 1, and was dissolved at 50 nM in a 1M NaCl/50 mM phosphate buffer solution (pH 7.0). The DNA chips subjected to the blocking reaction were immersed in the solution containing the labeled DNA for 2 hours at 45° C. Thereafter the unreacted DNA was washed away with a 1M NaCl/50 mM phosphate buffer solution (pH 7.0), followed by a rinsing with pure water.

(7) Result

The DNA chips subjected to the hybridization reaction were observed by using a fluorescent scanner (trade name: GenePix 4000B, manufactured by Axon Instruments, Inc.) at a wavelength of 532 nm. As a result, each spot was substantially circular with a diameter of 55 µm. When the fluorescence intensity of the spot of SEQ ID 1 probe at the center thereof was measured by using a PMT of 400 V and a laser power of 100%, the intensity of the DNA chip subjected to the UV irradiation was 6335, the intensity of the DNA chip not subjected to the UV irradiation was 21676. Also a background fluorescent intensity around the spot was 270 with the chip subjected to UV irradiation, and 383 with the chip not subjected to UV irradiation. In the foregoing, the deterioration of the probe by UV irradiation is judged from the fluorescent intensity.

When the UV labels were observed before the hybridization reaction, the UV label attached to the DNA chip not subjected to UV irradiation was white while that subjected to the UV irradiation had changed to pale pink. It proves that one can visually judge probe deterioration from the color change in the UV label. Table 1 summarizes the results of comparison of the fluorescent intensity with or without UV irradiation.

TABLE 1

| UV Irradiation Time | Fluorescent Intensity | Background |
| --- | --- | --- |
| 0 sec | 21676 | 383 |
| 5 sec | 6335 | 270 |

Example 2

Judgment of Probe Deterioration Caused by Ultraviolet Light (1) Preparation of DNA Chip A necessary number of DNA chips were prepared by a process similar to that in Example 1.

(2) Mounting of UV-Detecting Material

On each prepared DNA chip, a UV-label type-S (manufactured by Nichiyu Giken Kogyo Co.) was attached in a portion where the probe was not immobilized.

(3) UV Irradiation

DNA chips mounted with the UV detecting material in (2) were subjected to a UV irradiation for different times up to 10 seconds, with an irradiation amount of about 5 mJ/cm$^2$. Also control chips without UV irradiation were prepared.

(4) Preparation of Calibration Curve 1

Each UV label was scanned with a scanner (N-1240U, manufactured by Canon Inc.), and the color of the UV label was separated into RGB components of 256 levels each, and the G component was plotted as a function of the UV irradiation time. Results are shown in FIG. 1. As shown in FIG. 1, the G component intensity of the UV label linearly decreased as a function of the UV irradiation time.

(5) Preparation of Calibration Curve 2

Each DNA chip was subjected to blocking and hydridization reactions in the same manner as in Example 1 and then the fluorescent intensity was measured under the same conditions as in Example 1. Results are shown in Table 2.

TABLE 2

| UV irradiation time | fluorescent intensity |
| --- | --- |
| 0 sec | 21676 |
| 1 sec | 16638 |
| 5 sec | 6335 |
| 10 sec | 1029 |

Figure 2:
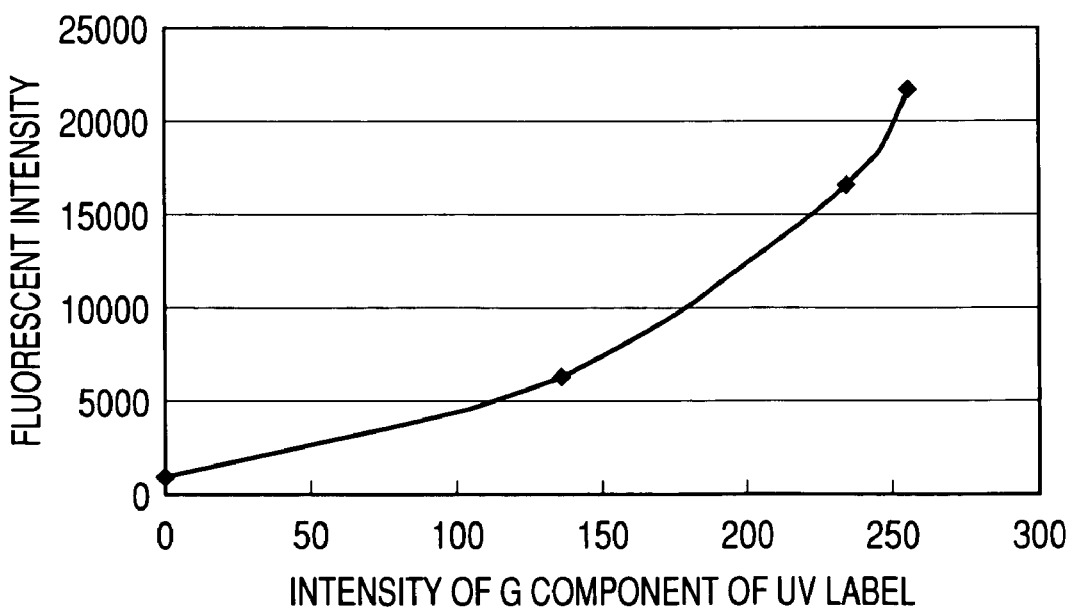
FIG. 2 shows a relationship between the G component intensity and the fluorescent intensity.

Based on the graph (calibration curve 1) showing the relationship between the G component and the UV irradiation time prepared in (4) and the relationship between the fluorescent intensity and the irradiation time obtained in (5), there was prepared a graph indicating a relationship between the G component and the fluorescent intensity. Result is shown in FIG. 2.

(6) Calculation of Probe Deterioration Level

A DNA chip mounted with the UV detecting material as shown in (2) was irradiated with ultraviolet light for 3 seconds, and the G component of the UV label measured as in (4) was 181. Based on the calibration curve shown in FIG. 2, the expected fluorescent intensity was about 11,000, and the probe deterioration level of this DNA chip was expected to be about 50%.

(7) Result

The DNA chip, subjected to the UV irradiation for 3 seconds in (6), was subjected to blocking and hybridization reactions in the same manner as in Example 1. As a result, there was obtained a fluorescent intensity of 11121. This proves that the level of probe deterioration can be calculated from the G component intensity of the UV label inversely proportional to the UV irradiation amount.

Example 3

Judgment of Probe Deterioration Caused by Temperature (1) Preparation of DNA Chip A necessary number of DNA chips were prepared by a process similar to that in Example 1.

(2) Mounting of Temperature-Detecting Material

On each prepared DNA chip, a cumulative temperature label KS90-20 (manufactured by Nichiyu Giken Kogyo Co.) was attached in a portion where the probe was not immobilized. This temperature label KS90-20 is white but irreversibly becomes brown with heating of 30 minutes at about 80° C., 20 minutes at about 90° C. or about 7 minutes at about 100° C.

(3) Heating

The DNA chips mounted with the temperature label described in (2) were separately subjected to heating of 50, 70 and 90° C. for 20 minutes in a clean oven.

Figure 3:
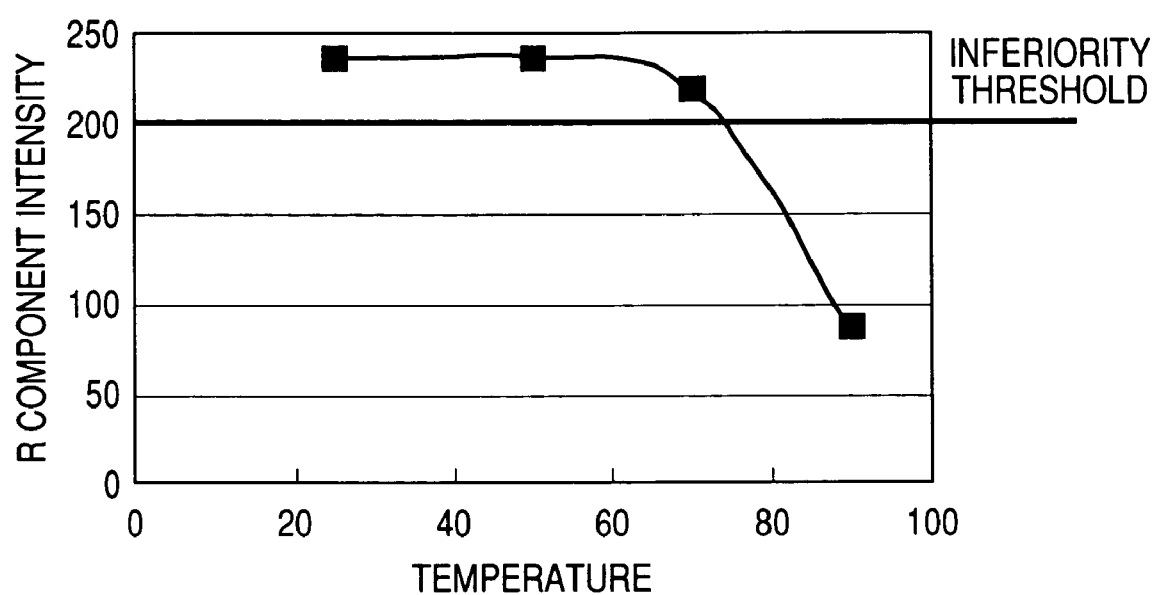
FIG. 3 shows a relationship between temperature and the R component intensity of a heat accumulation label.

Each temperature label was scanned with a scanner (N-1240U, manufactured by Canon Inc.), and the color of the temperature label was separated into RGB components of 256 levels each to know the relation ship between the R component and heating temperature. FIG. 3 shows a relationship between the heating temperature and the R component of the temperature label. The results indicate that the R component intensity rapidly decreased when the temperature exceeded 70° C. with 20 minute heating.

(4) Blocking Hybridization Reaction

The DNA chips subjected to heating or not were subjected to blocking and hybridization reactions in the same manner as in Example 1.

(5) Fluorescent Measurement

The DNA chips subjected to the hybridization reaction were observed by using a fluorescent scanner (trade name: GenePix 4000B, manufactured by Axon Instruments, Inc.) at a wavelength of 532 nm. As a result, each spot was substantially circular with a diameter of 55 μm. The fluorescent intensities measured using a PMT of 400 V and a laser power of 100% are shown in Table 3.

TABLE 3

| Temperature | R component | Fluorescent intensity | Probe deterioration rate (%) |
|---|---|---|---|
| 25° C. | 237 | 20650 | 0% |
| 50° C. | 236 | 17194 | 17% |
| 70° C. | 200 | 16311 | 20% |
| 90° C. | 85 | 14370 | 25% |

(6) Determination of Defective Level

If a chip deteriorated by 20% or more is defined as an inferior chip, Table 2 shows that the probe deterioration exceeds 20% when the R component becomes less than 200. This value is taken as an inferiority level.

(7) Sample Preparation

A temperature label KS90-20 was attached to a DNA chip prepared in the aforementioned method, and was subjected a heating 90°/3 minutes. The temperature label was scanned with a scanner, and the color of the temperature label was separated into RGB components of 256 levels each, and the R component was measured. The measured value was 204 which was higher than the aforementioned inferiority threshold, so that the level of probe deterioration was supposed to be 20% or less (acceptable level).

The DNA chip, subjected to heating of 90° C./3 minutes, was subjected to blocking and hybridization reactions in the same manner as explained above, and observed using a fluorescent scanner at a wavelength of 532 nm. The fluorescence intensity measured with PMT of 400 V and laser power of 100% was 17985 indicating an acceptable level of prove deterioration of 13%.

This proves that the temperature label, even when the heating period differs, can judge the level of probe deterioration without actually executing a hybridization reaction.

Example 4

Judgment of Change in Protective Member Caused by Temperature (1) Preparation of DNA Chip A necessary number of DNA chips were prepared by a process similar to that in Example 1.

(2) Solubilization of Polyvinyl Alcohol and Formation of Protective Member onto a Probe-Bearing Substrate.

5 g of polyvinyl alcohol (PVA103, manufactured by Kuraray Co., hydrolysis degree: 98.0 to 99.0 mol. %, polymerization degree: ca. 300) were weighed and added under agitation into 495 g of pure water in a beaker, thus dispersed in the pure water. Then polyvinyl alcohol was dissolved by heating for 1 hour at 80 to 90° C. on a hot water bath to obtain an aqueous PVA solution of a concentration of 1.0 wt. %. After cooling by standing, absence of undissolved substance was confirmed, and the solution was filtered through a 0.22 μm membrane filter to obtain a PVA solution.

The prepared DNA chip was immersed in the aqueous PVA solution for 30 seconds, then taken out and spontaneously dried. It is also possible, instead of such a coating method, to employ a spin coating method or a roll coating method, or to apply PVA to a probe-bearing portion of the probe-bearing substrate by an ink jet method or a pinning method.

(3) Mounting of Temperature-Detector

On each prepared DNA chip, a temperature label KS90-20 (manufactured by Nichiyu Giken Kogyo Co.) was attached in a portion where the probe was not immobilized. This temperature label KS90-20 is white but irreversibly becomes brown with heating of 30 minutes at about 80° C., 20 minutes at about 90° C. or about 7 minutes at about 100° C.

(4) Measurement of Protective Film Thickness

The film thickness of the prepared DNA chip determined by an ellipsometer (UVISEL, manufactured by Horiba Jobin Ybon Co.) was 203 Angstroms.

(5) Heating

The DNA chip provided with the protective film was left standing at 80° C. for 5 hours, and was then returned to the room temperature. The temperature label completely changed to brown.

(6) Dissolution of Protective Film

The DNA chip subjected to heating and the DNA chip not subjected to heating were respectively immersed for 10 minutes in a 1M NaCl/50 mM phosphate buffer solution (pH 7.0), then rinsed with pure water and spin dried.

(7) Thickness Measurement of Protective Film

The film thickness of the heated DNA chip, measured by the ellipsometer, was 153 Angstroms, while the film was not detected on the DNA chip not subjected to heating. This indicated that the protective member hardened by heating and could not be dissolved, and it was anticipated that the hybridization reaction could not be executed.

(8) Blocking Hybridization Reaction

The DNA chip subjected to heating and the DNA chip not subjected to heating were subjected to blocking and hybridization reactions in the same manner as in Example 1.

(9) Fluorescent Measurement

Fluorescence of the DNA chips subjected to the hybridization reaction or not were observed by using a fluorescent scanner (trade name: GenePix 4000B, manufactured by Axon Instruments, Inc.) at a wavelength of 532 nm. Fluorescence was not observed in the DNA chip subjected to heating. In the DNA chip not subjected to heating, each spot was substantially circular with a diameter of 55 μm. The fluorescent intensity measured with a PMT of 400 V and a laser power of 100% was 20139.

This proves that the change in the protective member can be determined by using a device for judging presence/absence of a change in the protective member, without actually carrying out the hybridization reaction.

The present invention have been explained by examples where the external factor was temperature or UV. As already described in the specification, however, it is possible to judge the level of probe deterioration with other factors in a simple manner based on the principle of the present invention.

The present invention is not limited to the above embodiments and various changes and modifications can be made within the spirit and scope of the present invention. Therefore to apprise the public of the scope of the present invention, the following claims are made.

This application claims priority from Japanese Patent Application No. 2003-387003 filed Nov. 17, 2003, which is hereby incorporated by reference herein.

change in a protective member which protects the probe of the probe-bearing substrate or both.

3. The method according to claim 1, wherein the device is one selected from an UV label and a temperature label.

4. The method according to claim 3, wherein the device is a temperature label.

5. A method for quantitatively determining a level of deterioration of a probe immobilized on a substrate, comprising:
  exposing the substrate having the probe immobilized thereon to an environment; and
  quantitatively determining the level of deterioration of the probe based on a color change of a device for detecting a cause of deterioration of the probe, using a calibration curve prepared in advance of the probe binding to a target substance by measuring the color change of the device and measuring a level of deterioration of the probe,
  wherein the device is attached to the substrate at a different position from the immobilized probe, and
  wherein the device detects an environmental change, the environmental change being at least one of a change in temperature and a change in exposure to ultraviolet light.

What is claimed is:

1. A method for determining an amount or presence/absence of a change in a probe-bearing substrate in which a nucleic acid probe capable of specifically binding to a target substance is immobilized on the substrate, the probe-bearing substrate further including a device for detecting an environmental change that causes the change in the probe-bearing substrate, the method comprising:
  exposing the probe-bearing substrate to an environment;
  measuring a color change of the device and a level of the change in the probe-bearing substrate in advance of the nucleic acid probe binding to the target substance; and
  determining the amount or presence/absence of the change in the probe-bearing substrate based on a level of the color change of the device,
  wherein the environmental change is at least one of a change in temperature and a change in exposure to ultraviolet light, and
  wherein the device is attached to the probe-bearing substrate at a different position from the immobilized probe.

2. The method according to claim 1, wherein the change in the probe bearing substrate is a deterioration in the probe, a 6. The method according to claim 5, wherein the device is one selected from an UV label and a temperature label.

7. A method for determining an amount or presence/absence of a change in a probe-bearing substrate in which a nucleic acid probe capable of specifically binding to a target substance is immobilized on the substrate, the probe-bearing substrate further including an UV label for detecting an environmental change that causes the change in the probe-bearing substrate, the method comprising:
  exposing the UV label to ultraviolet light;
  measuring a change of the UV label and a level of the change in the probe bearing-substrate in advance of the nucleic acid probe binding to the target substance; and
  determining the amount or presence/absence of the change in the probe-bearing substrate based on a level of the change of the UV label,
  wherein the UV label is attached to the probe-bearing substrate at a different position from the immobilized probe.

* * * * *

SEQUENCE LISTING

```
<160> NUMBER OF SEQ ID NOS: 1

<210> SEQ ID NO 1
<211> LENGTH: 18
<212> TYPE: DNA
<213> ORGANISM: Artificial
<220> FEATURE:
<223> OTHER INFORMATION: Test nucleic acid to be immobilized on
      substrate

<400> SEQUENCE: 1
actggccgtc gttttaca                                                    18
```